(12) United States Patent
Vogel et al.

(10) Patent No.: US 7,670,363 B2
(45) Date of Patent: Mar. 2, 2010

(54) PROTECTION APPARATUS FOR IMPLANTABLE MEDICAL DEVICE

(75) Inventors: Martin J. Vogel, Valencia, CA (US); Adam Vogel, legal representative, Valencia, CA (US); Richard J. Nelson, Canyon Country, CA (US); Robert A. Firth, Fraizer Park, CA (US); Anthony D. Falco, San Dimas, CA (US); Joseph H. Schulman, Santa Clarita, CA (US); Lung-Hsi Chu, Newhall, CA (US); Lee J. Mandell, West Hills, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 767 days.

(21) Appl. No.: 11/518,336

(22) Filed: Sep. 8, 2006

(65) Prior Publication Data
US 2007/0005111 A1 Jan. 4, 2007

Related U.S. Application Data

(60) Division of application No. 10/454,871, filed on Jun. 3, 2003, now abandoned, which is a continuation-in-part of application No. 10/420,070, filed on Apr. 18, 2003, now Pat. No. 7,108,711, which is a continuation-in-part of application No. 09/844,621, filed on Apr. 26, 2001, now Pat. No. 6,551,345.

(51) Int. Cl.
*A61N 1/08* (2006.01)

(52) U.S. Cl. .............................................. 607/1; 607/27
(58) Field of Classification Search .................. 206/438, 206/487, 488, 570, 706–719, 722, 724; 607/1, 607/27, 29, 36, 37
See application file for complete search history.

(56) References Cited

U.S. PATENT DOCUMENTS

| | | | | |
|---|---|---|---|---|
| 5,750,926 A | * | 5/1998 | Schulman et al. | 174/564 |
| 6,268,654 B1 | * | 7/2001 | Glenn et al. | 257/704 |
| 6,292,697 B1 | * | 9/2001 | Roberts | 607/27 |

* cited by examiner

*Primary Examiner*—Carl H Layno
*Assistant Examiner*—Frances P Oropeza
(74) *Attorney, Agent, or Firm*—Malcolm J. Romano

(57) ABSTRACT

A method and apparatus for protecting an electronic implantable medical device prior to it being implanted in a patient's body. The apparatus affords protection against electronic component damage due to electrostatic discharge and/or physical damage due to improper handling. The apparatus is comprised of a circuit board having conductive surface means for receiving and releasably grasping the electrodes of the medical device to support the device's housing proximate to the surface of the circuit board. First and second conductive paths are formed on the circuit board extending between the first and second conductive surfaces for shunting electrostatic discharge currents to prevent such currents from passing through the device's electronic circuitry. The respective shunt paths include oppositely oriented diodes, preferably comprising diodes which emit light (i.e., LEDs) when current passes therethrough. Additionally, means are provided to enable functional testing of the medical device.

22 Claims, 16 Drawing Sheets

PROTECTION APPARATUS FOR IMPLANTABLE MEDICAL DEVICE

This application is a divisional of U.S. patent application Ser. No. 10/454,871, filed Jun. 3, 2003, now abandoned which is a continuation-in-part of U.S. patent application Ser. No. 10/420,070, filed Apr. 18, 2003, now U.S. Pat. No. 7,108,711, which in turn is a continuation-in-part of U.S. patent application Ser. No. 09/844,621, filed Apr. 26, 2001, now U.S. Pat. No. 6,551,345.

FIELD OF THE INVENTION

This invention relates generally to a method and apparatus for use with an electronic implantable medical device for protecting the device from physical and/or electrostatic discharge damage prior to medically implanting the device in a patient's body. Moreover, preferred embodiments of the invention afford the ability to functionally test the device without removing it from its sterilized shipping container prior to implantation.

BACKGROUND OF THE INVENTION

Many types of electronic medical devices are known which are intended for implantation in a patient's body. Although these devices vary widely in design, they typically include a housing containing electronic circuitry connected to two or more electrodes which extend exteriorly from the housing (or one or more electrodes when the housing is the other electrode). The circuitry can, for example, include a functional circuit (e.g., a pulse generator), a power supply circuit (e.g., rechargeable battery), and a transceiver for wirelessly communicating with an external controller. Implantable medical devices of this sort are useful in a variety of applications for stimulating muscle or nerve tissue and/or monitoring body parameters. See, for example, U.S. Pat. Nos. 6,164,284; 6,185,452; 6,208,894; 6,315,721; and 6,472,991; which primarily relate to such devices that are battery powered, each of which is incorporated by reference herein in their entirety. Also see, for example, U.S. Pat. Nos. 5,193,539; 5,193,540; 5,312,439; 5,324,316; and 5,405,367; which primarily relate to such devices that are RF powered, each of which is incorporated by reference herein in their entirety.

To minimize device failure and maximize device reliability, it is important that an electronic medical device be properly handled along the entire chain from manufacturing, through shipping and storage, and on to the medical procedure for implanting the device in a patient's body. For example, improper handling can subject the device to physical damage and/or component damage due to electrostatic discharge (ESD).

SUMMARY OF THE INVENTION

The present invention is directed to a method and apparatus for protecting an electronic implantable medical device prior to it being implanted in a patient's body. More particularly, a method and apparatus in accordance with the invention affords protection to the medical device from just after manufacture to just prior to implantation. Protection is afforded against electronic component damage due to electrostatic discharge and/or physical damage due to improper handling.

Embodiments of the invention are particularly valuable when used with small fragile medical devices which often comprise an electronic circuit housing having an axial dimension of less than 60 mm and a lateral dimension of less than 6 mm. The housing typically contains electronic circuitry which is electrically connected to first and second electrodes which extend exteriorly from the housing. See, for example, U.S. Pat. Nos. 6,164,284; 6,185,452; 6,208,894; 6,315,721; and 6,472,991; which primarily relate to such devices that are battery powered, each of which is incorporated by reference herein in their entirety. Also see, for example, U.S. Pat. Nos. 5,193,539; 5,193,540; 5,312,439; 5,324,316; and 5,405,367; which primarily relate to such devices that are RF powered, each of which is incorporated by reference herein in their entirety.

A preferred apparatus in accordance with the invention is comprised of a circuit board having first and second connective surfaces integral to the circuit board. The connective surfaces are configured using elastic O-rings to receive and releasably grasp the electrodes of a medical device housing to support the housing proximate to the surface of the circuit board. First and second conductive paths are formed on the circuit board extending between the first and second connective surfaces for shunting electrostatic discharge currents to prevent such currents from passing through the device's electronic circuitry. Preferably, the respective shunt paths include oppositely oriented diodes, preferably comprising diodes which emit visual light (i.e., LEDs) when current passes therethrough.

In accordance with the invention, a medical device is preferably mounted in the protective apparatus as a late step in the device manufacturing process. The protection apparatus/device combination is then placed into a shipping container. The combination remains engaged until the device is ready for medical implantation in a patient's body. The shipping container preferably includes a transparent window through which the light emitting diodes are visible.

In a preferred method in accordance with the invention, the medical device is sterilized, e.g., using steam or ethylene oxide (ETO), after being placed in the shipping container.

A significant feature of the invention allows the medical device to be functionally tested while in the shipping container. More particularly, exemplary medical devices include (1) transceivers which permit wireless communication of commands and data between an external controller and the device electronic circuitry and (2) battery charging circuits which extract energy from an external power source, e.g., via an alternating magnetic field, for charging a device battery. In accordance with the invention, a medical device can be functionally tested while still in the shipping container by transmitting a command or activation signal to the device. If the device is functioning properly, it will respond in a particular manner, as by outputting a sequence of pulses whose characteristics (e.g., frequency, pulse width, etc.) indicate proper operability. This output pulse sequence drives the protection apparatus LEDs which can be monitored to detect whether the device is operating within specifications. Additionally, the device battery can be charged while still in the shipping container by an external power source.

In a still further significant aspect of the present invention, a cutout is provided in the circuit board to permit a wire loop from an oscilloscope, pulse generator, or the like, to pass through and inductively measure/induce the electrical input/output characteristics of the medical device before implantation. A sealing pouch preferably has a conforming cutout to facilitate this test while maintaining the medical device in a sterilized environment. Alternatively and/or additionally, a photodiode may be placed on the circuit board to emit non-visual radiation that may be sensed by an external detection apparatus to measure the electrical output characteristics of the medical device. Finally, the output characteristics of the medical device may be measured using external capacitively coupled plates and/or one or more coils.

BRIEF DESCRIPTION OF THE DRAWINGS

FIGS. 13A and 13B show the presence of the current loop path described in reference to FIG. 12 with a cutout for allowing the oscilloscope probe loop to pass through.

DETAILED DESCRIPTION OF THE PREFERRED EMBODIMENTS

Figure 1:
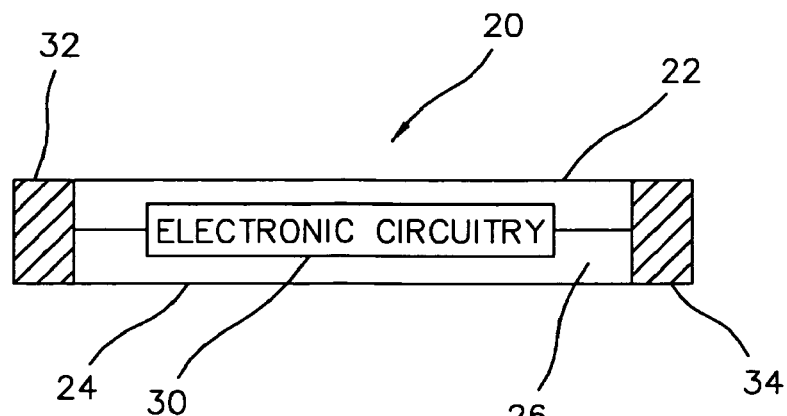
FIG. 1 schematically depicts the structure of an exemplary electronic implantable medical device of the type intended for use with the present invention.

Attention is initially directed to FIG. 1 which schematically depicts an electronic implantable medical device 20. The device 20 is intended to be representative of a wide range of known electronic devices designed to be medically implanted in a patient's body for a variety of applications. For example only, such devices can be controlled to selectively stimulate muscle and nerve tissue and/or monitor and report various body parameters. The exemplary device 20 is depicted as comprising an elongate housing 22 defined by a peripheral wall 24 enclosing an interior volume 26. The housing 22 can be variously shaped but, for simplicity herein, it will be assumed to be cylindrical. Typically such implantable medical devices are small in size, e.g., preferably having an axial dimension of less than 60 mm and a lateral dimension of less than 6 mm, and relatively fragile structurally. See, for example, U.S. Pat. Nos. 6,164,284; 6,185,452; 6,208,894; 6,315,721; and 6,472,991; which primarily relate to such devices that are battery powered, each of which is incorporated by reference herein in their entirety. Also see, for example, U.S. Pat. Nos. 5,193,539; 5,193,540; 5,312,439; 5,324,316; and 5,405,367, which primarily relate to such devices that are RF powered, each of which is incorporated by reference herein in their entirety. Reasonable care must be exercised in handling the devices 20 to prevent physical damage.

The exemplary device 20 is depicted as containing electronic circuitry 30 within the interior volume 26. The circuitry 30 is connected between first and second electrodes 32, 34 which extend exteriorly from the housing 22. The circuitry 30 typically includes sensitive electronic components which can be permanently damaged by high currents which can be caused, for example, by electrostatic discharge (ESD). Accordingly, as with many other electronic devices, it is advisable to exercise appropriate care to avoid discharging high currents through the circuitry 30. The present invention is primarily directed to a method and apparatus as depicted in FIGS. 3-15, for protecting the device 20, from damage while being shipped, stored, and handled between a late manufacturing stage and up to the time it is implanted in a patient's body.

Figure 2:
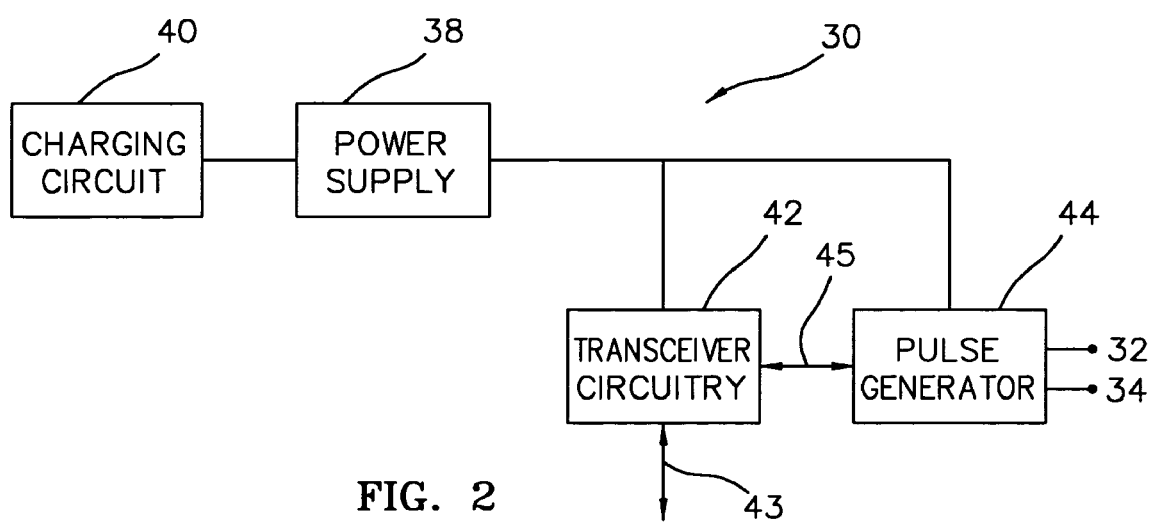
FIG. 2 is a block diagram generally representing the electronic circuitry typically employed in the exemplary medical device of FIG. 1.

FIG. 2 is a block diagram which generally depicts the functional components of typical electronic circuitry 30 employed in an implantable medical device 20. More particularly, the electronic circuitry 30 is shown as comprising a power supply 38 which may include a rechargeable battery or a capacitor (not shown). A charging circuit 40 is connected to the power supply 38 for deriving energy from an external power source to charge the battery. For example only, the charging circuit 40 can respond to an alternating, e.g., amplitude modulated or frequency modulated, magnetic field or RF field to supply a charging current to the power supply 38. The power supply 38 is depicted as supplying an operating voltage to a transceiver circuitry 42 and a pulse generator 44. The transceiver circuitry 42 is configured to communicate with an external controller (not shown) employing a suitable form of wireless communication via path 43, typically radio communication. Commands and data can be supplied via path 43 from the external controller to the transceiver circuitry 42 for controlling or programming the pulse generator 44. The pulse generator 44 can in turn provide data to the transceiver circuit 42 via path 45 for communication to the external controller.

It should be understood that FIG. 2 is intended to only very generally depict the functionality of the electronic circuitry 30 contained in the device 20. The method and apparatus of the invention to be described herein, is useful in combination with a wide variety of medical devices 20, e.g., muscle stimulators, neural stimulators, physiological sensors, pacemakers, etc.

Figure 3:
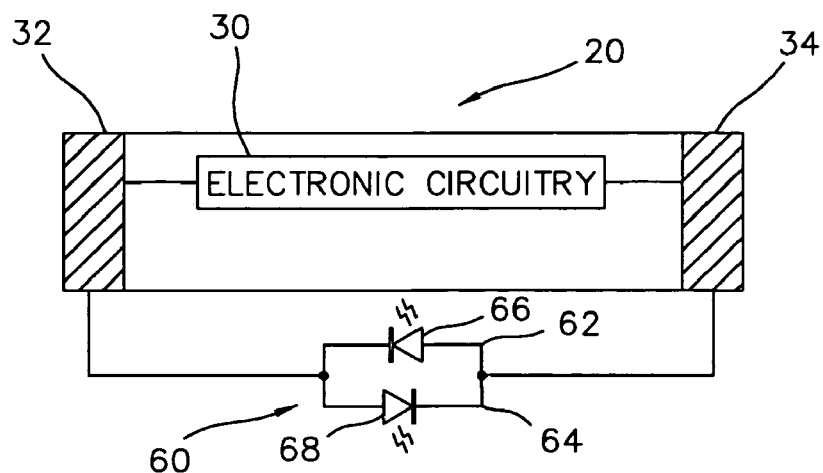
FIG. 3 schematically depicts the exemplary medical device of FIG. 1 used in combination with a protection apparatus in accordance with the present invention.

Attention is now directed to FIG. 3 which depicts an electronic protection circuit 60 externally connected between the device electrodes 32, 34. The protection circuit 60 is comprised of first and second shunt paths 62, 64 which each include a unidirectional current device, e.g., a diode. Shunt path 62 contains diode 66 oriented from electrode 32 to electrode 34. Shunt path 64 contains diode 68 which is oppositely oriented, i.e., from electrode 34 to electrode 32. The shunt paths 62 and 64 operate to shunt current spikes which can be caused, for example, by electrostatic discharge around electronic circuitry 30. Thus, the shunt paths limit excessive currents and voltage rise across the medical device 20.

As will be discussed hereinafter, the diodes 66, 68 preferably have an audible or light generator associated therewith to indicate current therethrough. More specifically, preferred embodiments of the invention are preferably implemented with light emitting diodes (LEDs). As will be understood hereinafter, it is preferable for the respective LEDs to produce light of different colors so that the direction of current flow between electrodes 32 and 34 can be readily determined by an observer.

Figure 4:
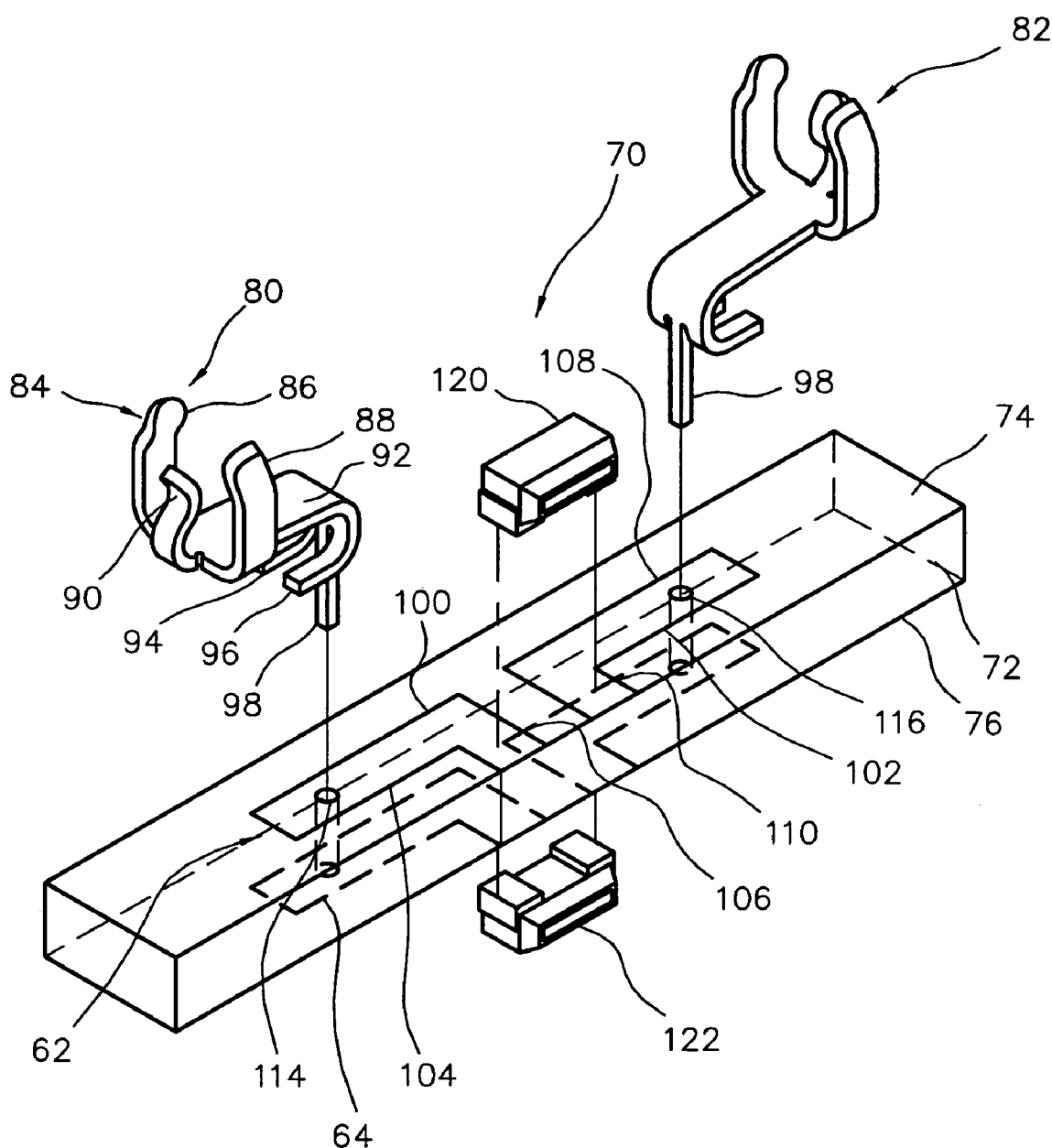
FIG. 4 is an exploded isometric illustration depicting a protection apparatus in accordance with the present invention.

FIG. 4 depicts a preferred implementation of a protection apparatus 70 in accordance with the present invention tailored for use with the exemplary cylindrical medical device 20. The apparatus 70 is comprised of a substrate or circuit board 72 having an upper surface 74 and a lower surface 76.

First and second spring contact clips 80, 82 are provided for mounting on the circuit board 72. Each clip is essentially comprised of a cradle portion 84 including spaced first and second resilient arms 86, 88. The arms 86, 88, together with end finger 90, define a cradle for releasably retaining an electrode 32, 34 of device 20. The cradle portion 84 is cantilevered by a shank portion 92 which extends to spaced contact fingers 94, 96 and to a post 98. The clips 80, 82 can be inexpensively formed by a stamping and bending operation.

The circuit board 72 has shunt path 62 formed on upper surface 74 depicted as including path portion 100 and path portion 102. Path portion 100 is comprised of a longitudinal leg 104 and a lateral leg 106. Similarly, path portion 102 is comprised of a longitudinal leg 108 and a lateral leg 110. The clips 80 and 82 are respectively mounted onto the board 72 with the posts 98 extending into and electrically contacting through plated apertures 114 and 116 in path legs 104 and 108. The through plated apertures extend and are electrically connected to a second shunt path 64 formed on the opposite lower surface 76 of circuit board 72. The shunt path 64 on the surface 76 can be shaped identically to the shunt path 62 on upper surface 74 depicted in FIG. 4. The post 98 of clip 80 extending through the aperture 114 electrically interconnects the first ends of shunt paths 62 and 64. Similarly, the post 98 of clip 82 extending through aperture 116 electrically interconnects the second ends of shunt paths 62 and 64. Each shunt path includes a diode as depicted in FIG. 4. More particularly, note that LED 120 is configured to be surface mounted across legs 106 and 110 of shunt path 62 on board surface 74. Similarly, LED 122 is intended for corresponding surface mounting in shunt path 64 on board surface 76. Alternatively, LEDs 120, 122 may be mounted on the same surface of the circuit board 72.

Figure 5:
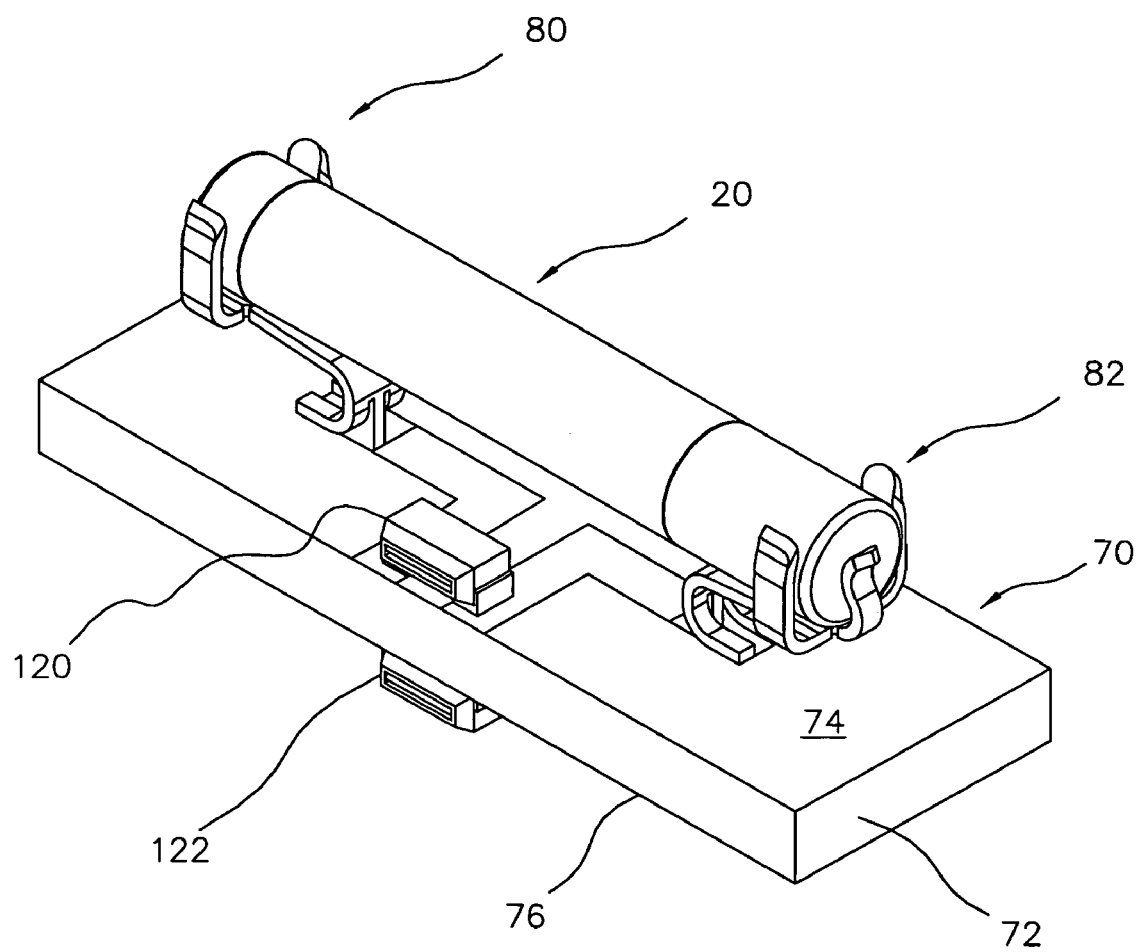
FIG. 5 is an isometric illustration depicting a protection apparatus in accordance with the present invention for accommodating a medical device to be protected.
Figure 6:
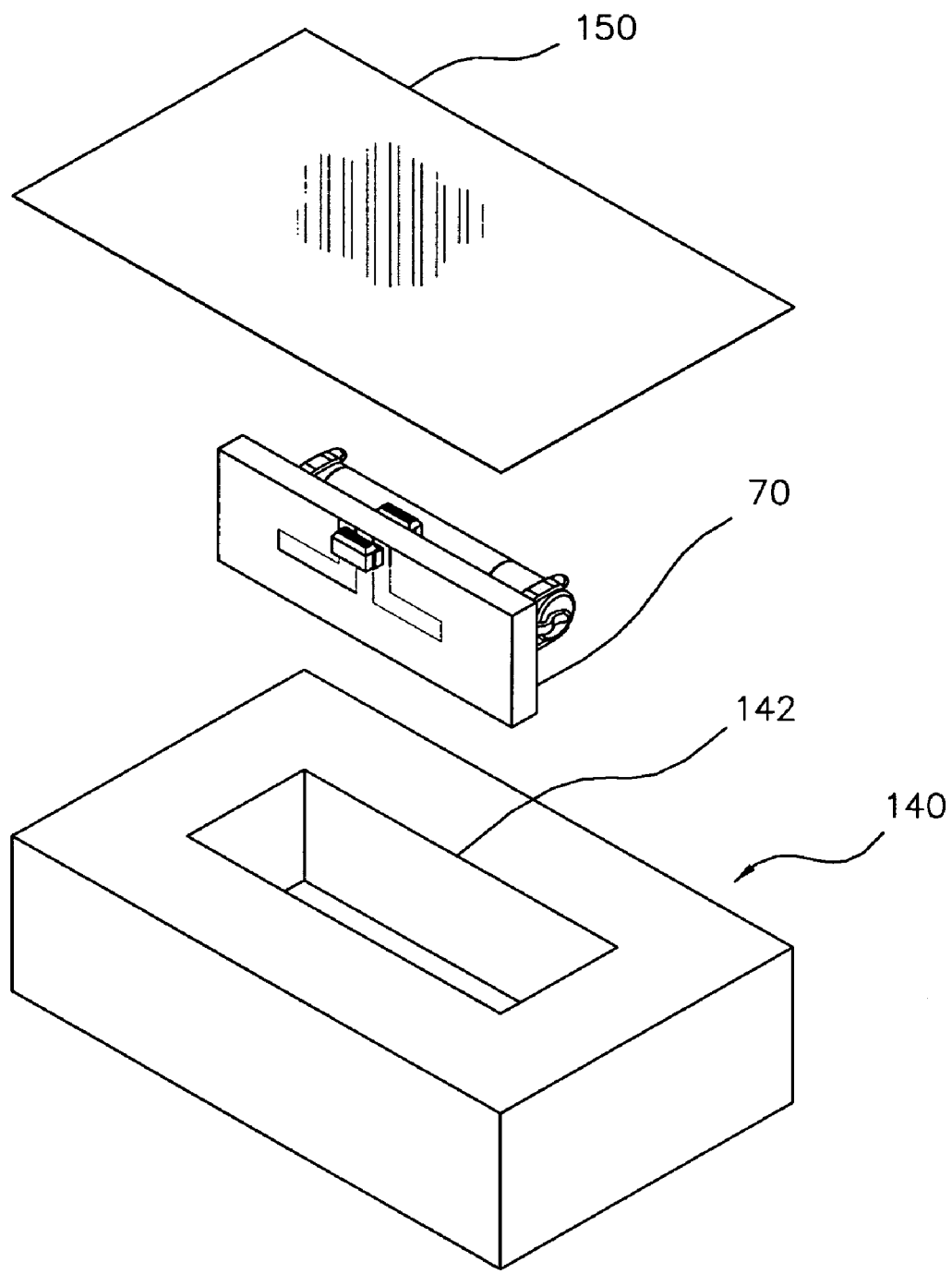
FIG. 6 is an exploded isometric illustration depicting the manner of placing the protection apparatus and medical device into an exemplary shipping container.
Figure 7:
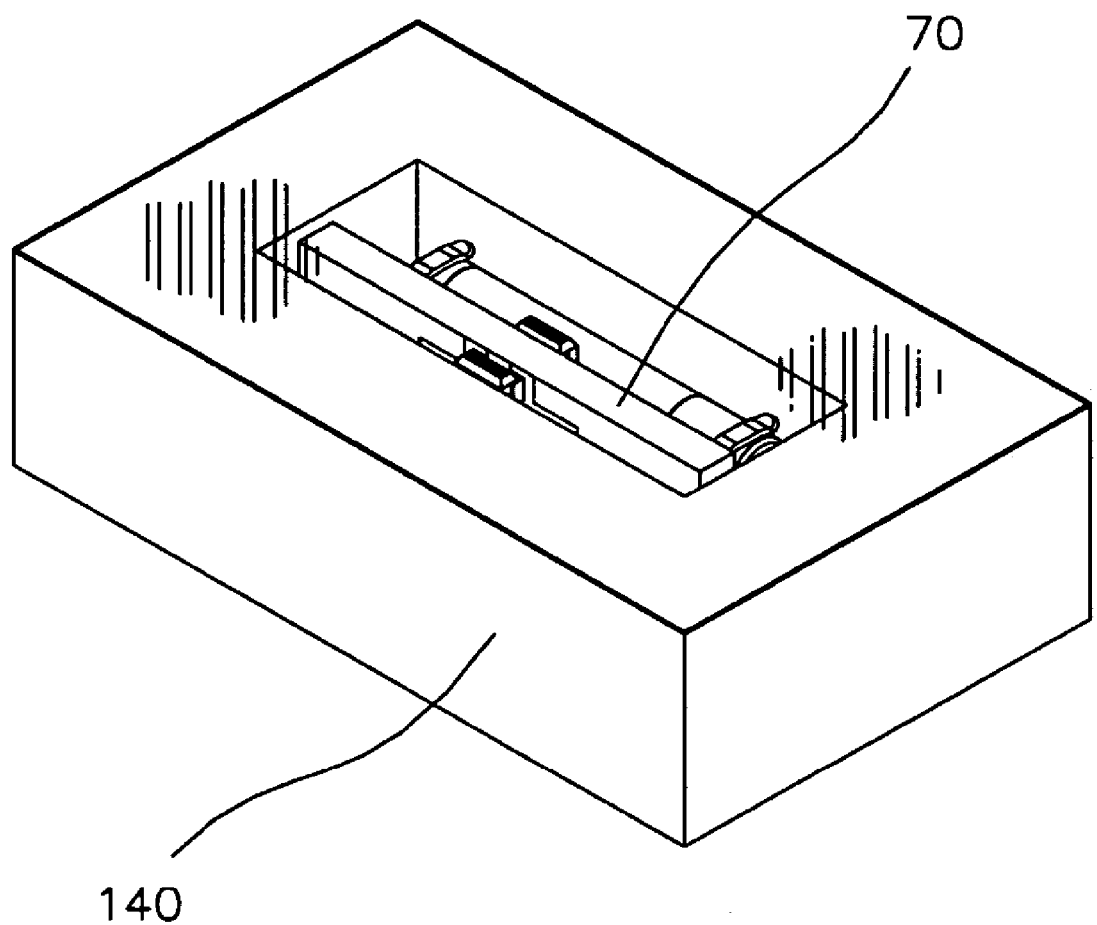
FIG. 7 is an isometric view depicting the protection apparatus and medical device received in the exemplary shipping container and oriented so that the light emitting diodes (LEDs) of the apparatus are visible through a container transparent window.

FIG. 5 shows the medical device 20 accommodated in the clips 80 and 82 and with the LEDs 120, 122 being mounted on opposite surfaces 74 and 76 of circuit board 72. In accordance with the invention, the device 20 is mounted into the clips 80, 82 in a late stage of the manufacturing process of device 20. Thereafter, the mated protection apparatus 70 and medical device 20 are placed in a shipping container 140, as depicted in FIG. 6. Shipping container 140 can be inexpensively formed of molded plastic, and preferably includes a cavity 142 shaped and dimensioned to accommodate the mated protection apparatus 70 and medical device 20. In placing the mated combination in the cavity, circuit board 72 should be oriented so that the LEDs 120 and 122 face upwardly. A transparent sheet 150 covers the cavity 142, to define a window through which the LEDs 120 and 122 are visible as depicted in FIG. 7.

It is intended that the protection apparatus 70 and medical device 20 remain mated together in the shipping container 140 for the full duration of its shelf life from the manufacturing stage to just prior to medically implanting the device 20 in a patient's body. After the mated protection apparatus and medical device 20 are placed into the shipping container 140 and the cavity 142 sealed by transparent sheet 150, the device 20 is preferably sterilized using a known gas, e.g., ethylene oxide (ETO), or steam process. For its entire life between manufacturing and implantation, the protection apparatus 70 will protect the medical device from electronic component damage attributable to electrostatic discharge (ESD). Moreover, the apparatus 70 protects device 20 against physical damage because it is firmly retained by spring clips 80, 82 mounted on the substantially rigid circuit board 72.

Figure 8:
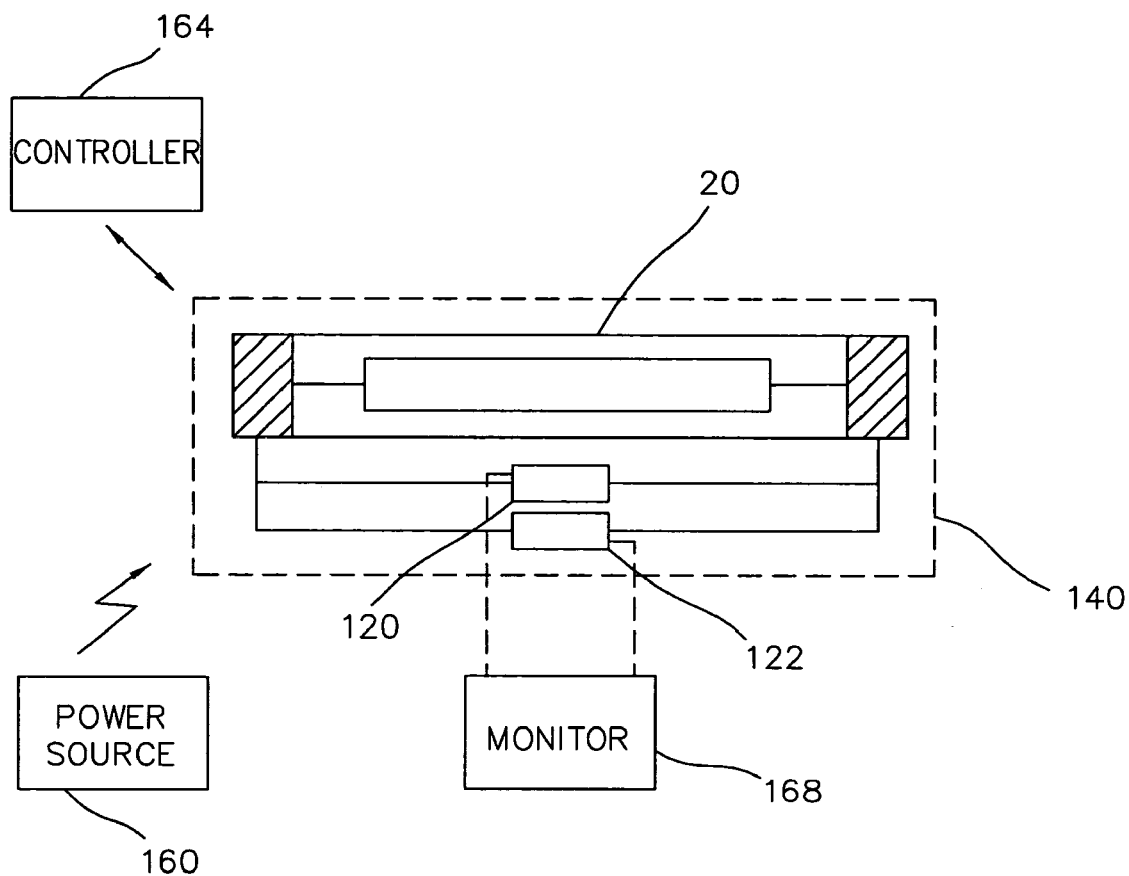
FIG. 8 is a block schematic diagram depicting how the medical device is tested while in the exemplary shipping container.

In accordance with the present invention, the device 20 is preferably functionally tested while still in its shipping container 140. More particularly, as depicted in FIG. 8, an external power source 160 is able to charge the on-board device battery via the aforementioned charging circuit 40 by generating an appropriate field, e.g., alternating magnetic field, in close proximity to the device 20. The power source 160 can be similar or identical to the power source normally used to charge the battery after the device is implanted in a patient's body. Similarly, an external controller 164 can be used to provide commands and receive data from the medical device 20 while it is still contained within the shipping container 140. In a particularly useful procedure, the controller 164 is able to wirelessly communicate a command or activation signal to the device 20, e.g., via an RF signal. The controller 164 can be similar or identical to a controller utilized by the patient or by a medical practitioner to program the device 20 after implantation in the patient's body. The procedure depicted in FIG. 8 contemplates that the controller 164 provides an activation signal to the medical device 20 while it is still in the shipping container 140. The electronic circuitry of the device 20 is designed to respond to the activation signal to cause pulse generator 44 to output a known pulse sequence between electrodes 32 and 34. This pulse sequence will cause LEDs 120 and 122 to illuminate in accordance with a pattern having known characteristics (e.g., frequency, pulse width, etc.). The activity of the LEDs 120 and 122 can be monitored by monitor 168 to determine whether the device 20 is operating properly. For example, if the device 20 is configured to generate monophasic pulses, one LED will "brightly" light during generation of each pulse and the other LED will "dimly" light during recharge of the pulse generator 44. Alternatively, if the device 20 is configured to generate a biphasic pulse, the intensity of the light emitted from each LED will be approximately the same.

Thus, it will be appreciated that the protection apparatus 70 in accordance with the present invention offers both electrical and physical protection of the device 20 during shipping and handling, and facilitates the testing of the device prior to it being medically implanted in a patient's body.

It is important that medical devices intended for implantation in a patient's body be biocompatible, i.e., that they employ materials which do not produce deleterious effects on the living tissue. This requirement dictates a choice of appropriate biocompatible materials. In order to avoid compromising biocompatibility, it is preferable that the contact clips 80, 82 which physically contact the electrodes 32, 34 of the device 20 also be formed of an appropriate biocompatible material, e.g., platinum.

Figure 9A:
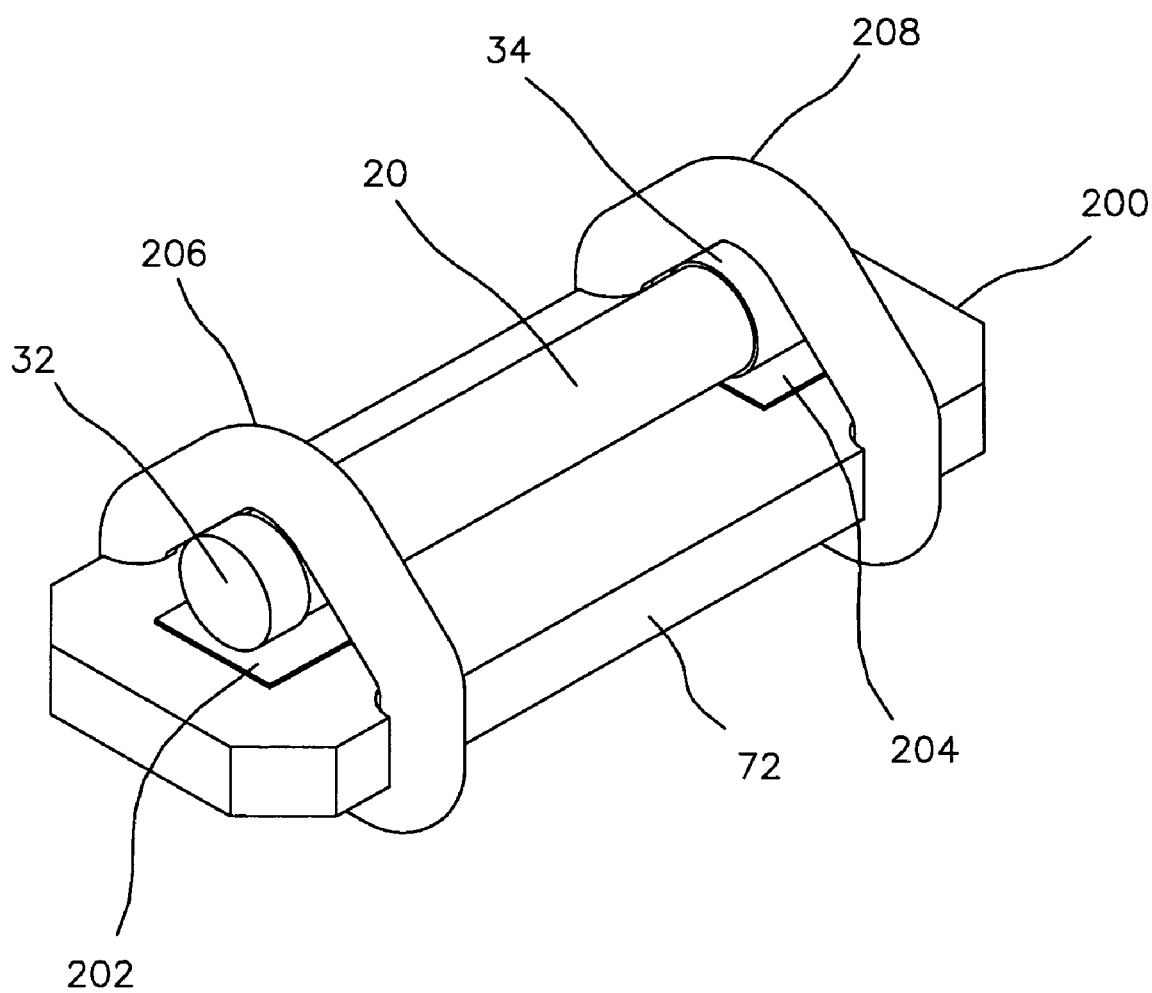
FIGS. 9A and 9B show isometric views of the mounting of the medical device on a planar surface having a pair of connective surfaces for making electrical contact with the electrodes of the medical device and a pair of O-rings for retaining physical and electrical contact between the medical device's electrodes and the circuit board's connective surfaces.
Figure 9B:
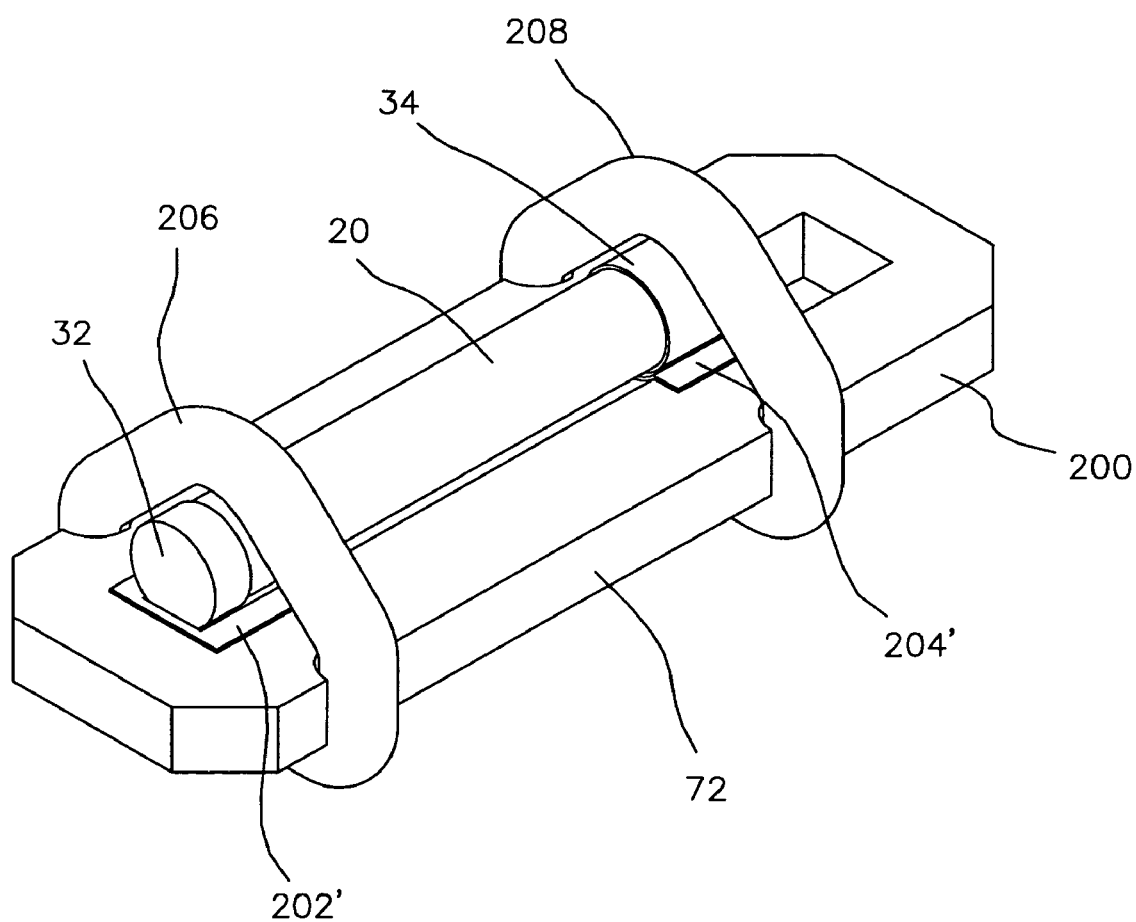

FIGS. 9A and 9B show isometric views of the mounting of the medical device 20 on a planar surface 200 having a pair of connective surfaces 202, 204 for making electrical contact with the electrodes 32, 34 of the medical device 20 and a pair of O-rings 206, 208 (preferably formed from medical grade silicone) for physically retaining and maintaining electrical contact between the medical device's electrodes 32, 34 and the circuit board's connective surfaces 202, 204. In this embodiment, the use of O-rings 206, 208 functionally replace the previously described use of clips 80, 82 while further minimizing any potential for damage to protective gloves worn by medical practitioners when working with the sterilized and packaged medical device 20. The O-rings 206, 208 are easily rolled onto the ends of the circuit board 72 until they hold the medical device 20 into contact with the connective surfaces 202, 204. Since the package must be subject to high temperatures for sterilization purposes, the planar surface 20, e.g., circuit board 72, is formed of polyimide or like material that can withstand the temperatures associated with sterilization. The connective surfaces are preferably formed from a biocompatible material, e.g., platinum or gold plated nickel on copper to provide a surface that will minimize electrical resistance to the medical device's electrodes while maintaining biocompatible safety should the gold or platinum slough off onto the electrodes 32, 34. FIG. 9B, in particular, shows two optional means that may be used to stabilize the position of the medical device 20 on the connective surfaces. In this example, connective surface 202' is shown with a recess, e.g., a concave portion, and connective surface 204' is shown with a notched portion, each of which are exemplary of optional techniques for stabilizing the medical device's position. Clearly, each of these techniques could be used on both ends of the medical device and the use of different techniques for each electrode is primarily for illustrative purposes to minimize the number of provided figures.

Figure 10A:
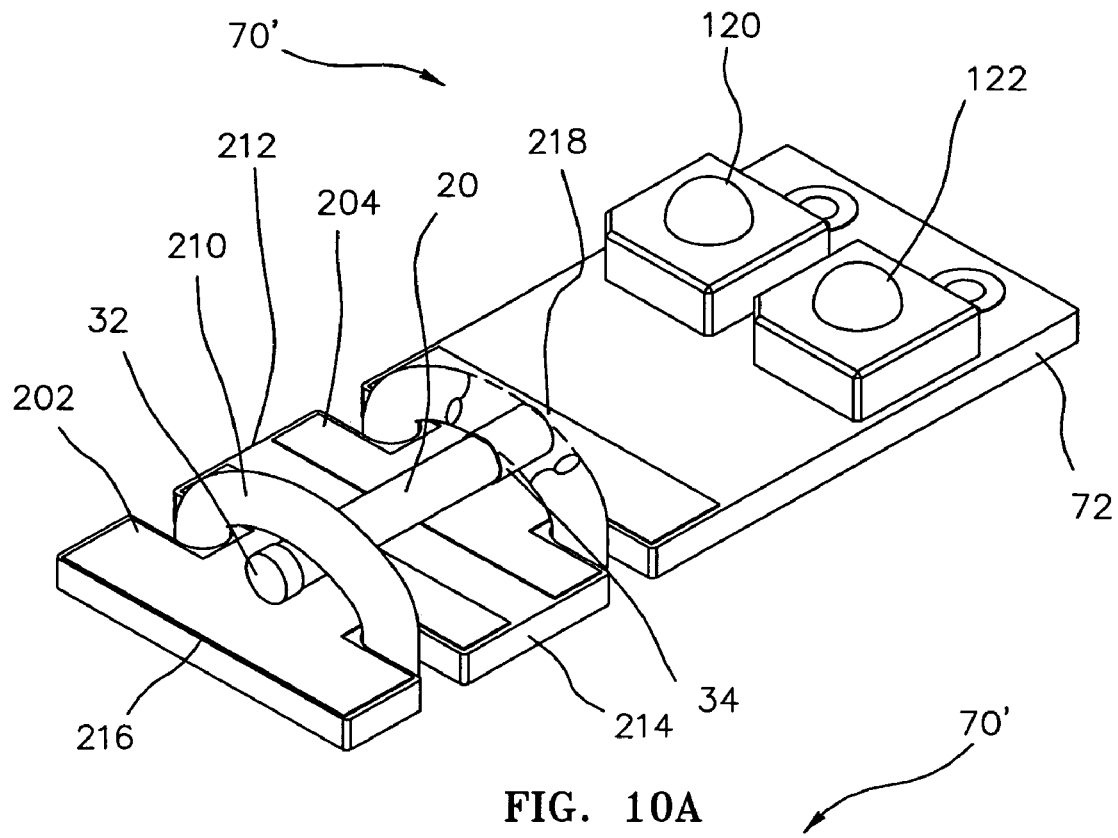
FIGS. 10A and 10B show isometric views of the mounting of the medical device on a planar surface having a pair of connective surfaces for making electrical contact with the electrodes of the medical device and a single O-ring for retaining physical and electrical contact between the medical device's electrodes and the circuit board's connective surfaces.
Figure 10B:
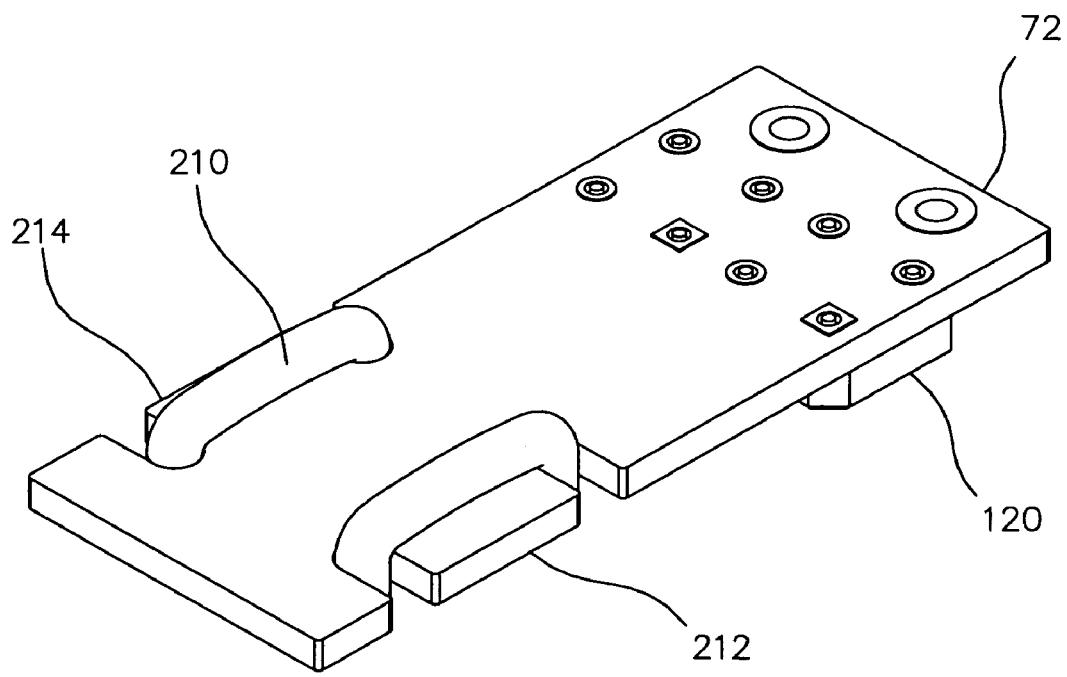

FIGS. 10A and 10B (a variation of that already shown and described in relation to FIGS. 9A and 9B) show isometric views of the mounting of the medical device 20 on a planar surface 200 having a pair of connective surfaces 202, 204 for making electrical contact with the electrodes 32, 34 of the medical device 20 with a single O-ring 210 for retaining physical and electrical contact between the medical device's electrodes and the circuit board's connective surfaces 202, 204. In this embodiment, the circuit board 72 is formed with a pair of opposing retaining lips 212, 214 for retaining/capturing opposing ends of the O-ring 210. In operation, the O-ring 210 is typically initially captured by the two retaining lips 212, 214 and when the medical device 20 is available it is slipped between the O-ring 210 and the circuit board 72 from the outside end 216 of the circuit board 72 until its electrodes 32, 34 line up with the connective surfaces 202, 204. Due to the relatively large size of the connective surfaces 202, 204 to the electrodes 32, 34, this positioning is easily performed. Optionally, a stop may be placed on connective surface 204 at location 218 to block further inner movement of the medical device 20 during insertion into the protection apparatus 70' (see FIG. 10A). Alternatively, the medical device 20 may be placed on the circuit board 72 and the single O-ring 210 may be stretched and captured between the two retaining lips 212, 214. Functionally, e.g., as pertaining to protection and test features, the apparatus described in relation to FIGS. 9A, 9B, 10A, and 10B performs as previously described in relation to FIGS. 4 and 5.

FIGS. 3-8, 10A and 10B, primarily show a protection apparatus whose output drivers may also be functionally tested (generally in response to received communication signals) by visually (or automatically, see monitor 168 in FIG. 8) monitoring the response of its LEDs 120 and 122 when the medical device 20 is commanded to generate stimulation pulses. While this is an effective functional test, its capability to measure actual performance characteristics, e.g., the milliamp output, of the medical device 20 is limited. Accordingly, FIGS. 11-15 are primarily directed to alternative embodiments that additionally provide the capability to measure, albeit, indirectly the performance characteristics of the medical device 20 prior to implantation. The requirement to indirectly measure these characteristics is dictated by the requirement that the medical device 20 be maintained within a sterile package before implantation. The description of various techniques follows, including (1) the use of a photodiode and associated photodetector (and transconductance amplifier) to provide a relatively linear measurement of the output of the medical device, (2), the use of an inductive current loop with an associated cutout in the circuit board of the protection apparatus to accept a receiving inductive pickup loop, e.g., connected to an oscilloscope or the like, to measure the output of the medical device, (3) the use of an inductive current loop with an associated cutout in the circuit board of the protection apparatus to accept a transmitting inductive current loop driven by an external pulse generator or the like to provide an input signal, e.g., a simulated neuro-muscular signal, and thus allow the sense circuitry of the medical device to be tested, etc. These techniques may be used in various combinations but what is significant is that they all provide test/measurement capabilities while the medical device is still within its sterile delivery package, e.g., a pouch.

Figure 11:
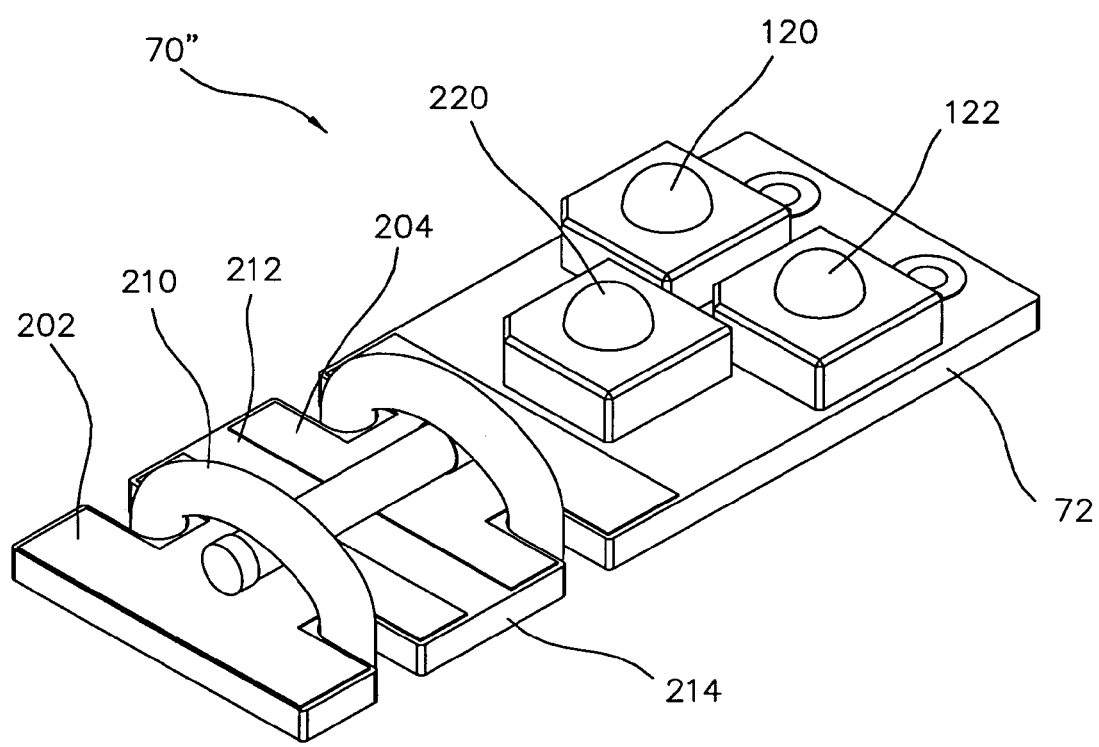
FIG. 11 shows an isometric view of the circuit board and O-ring mounting apparatus of FIGS. 10A and 10B, additionally including a photodiode for emitting nonvisual radiation that can be externally monitored to test the functionality of the medical device, e.g., while it is still within a sterilized container, e.g., a pouch.
Figure 12:
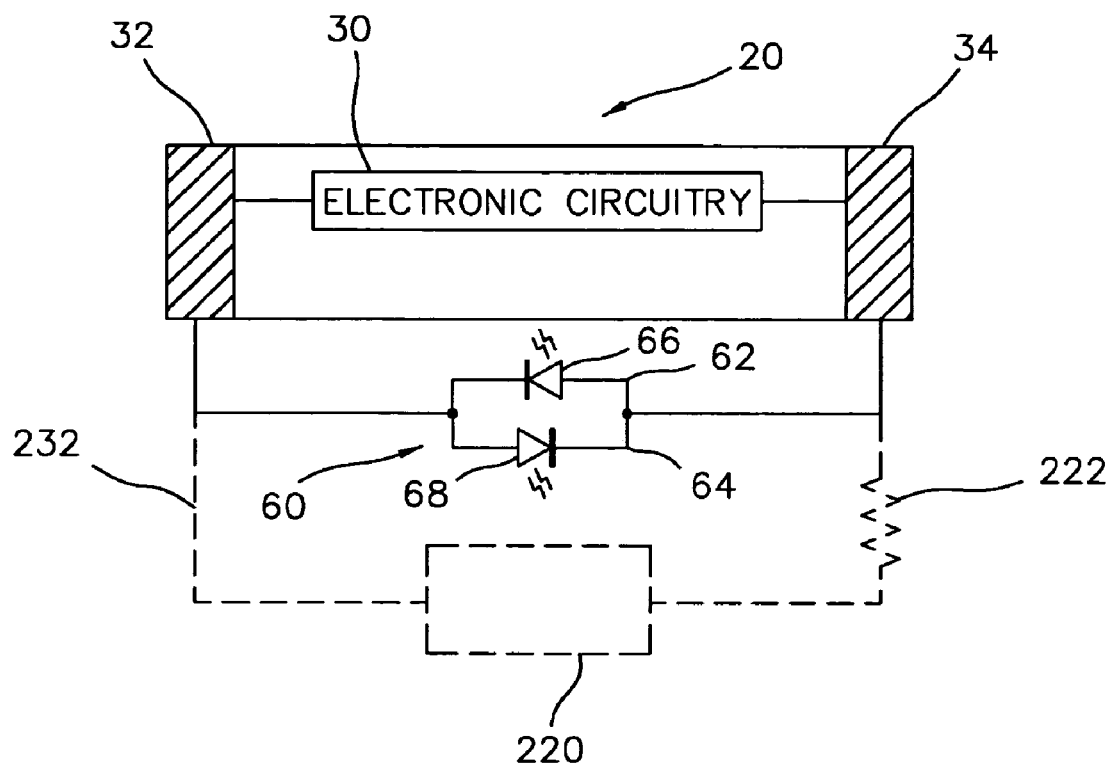
FIG. 12 shows a simplified schematic diagram of additional embodiments of the present invention that include the photodiode of FIG. 11 and/or a current loop path that may be used to emit an inductively coupled field to a loop connected to an oscilloscope probe or the like. Alternatively, a pulse generator of the like may be used to inductively emit a signal into the loop on the circuit board and thus verify the functionality of the sensor mode circuitry in the medical device.
Figure 15:
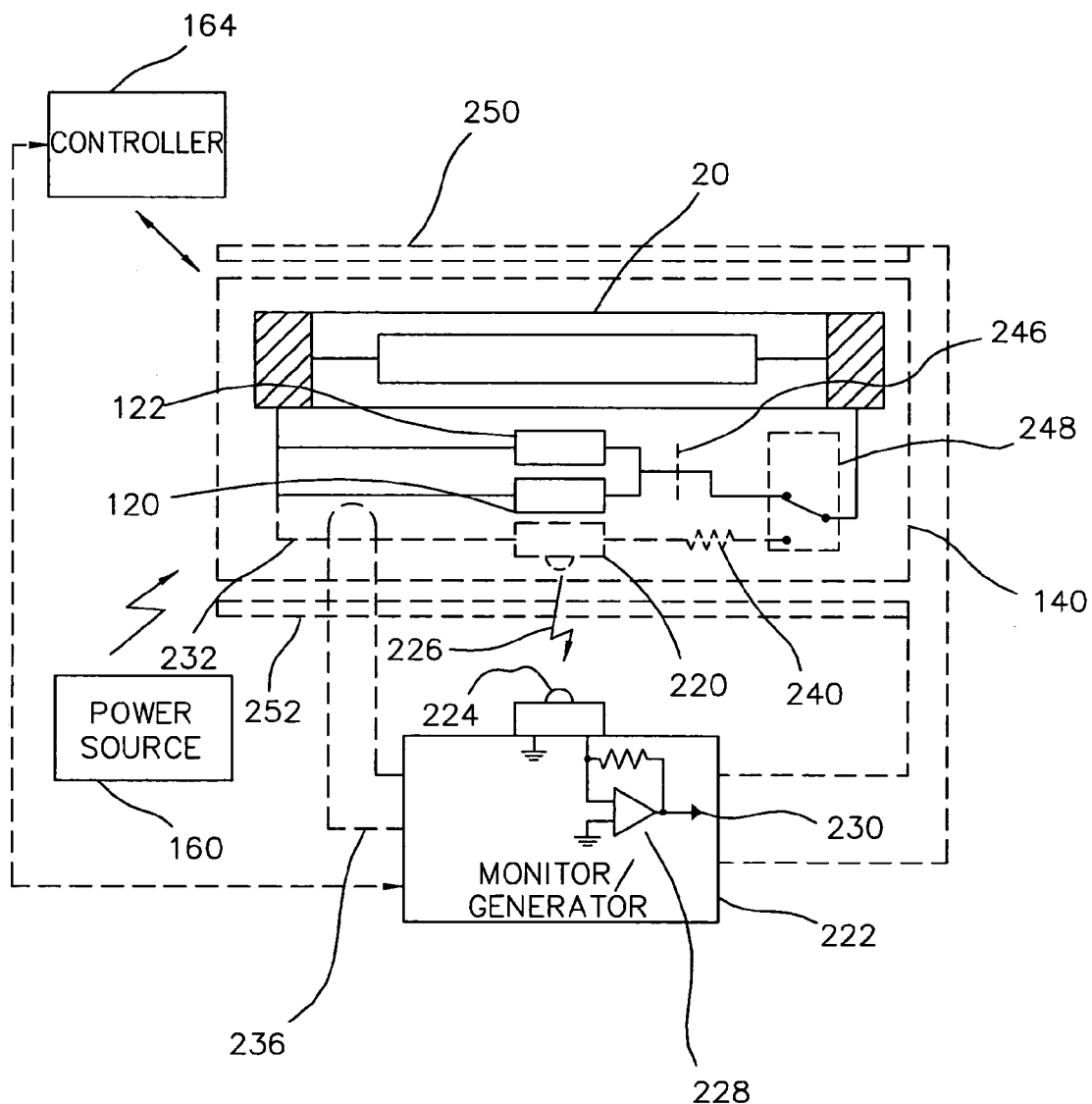
FIG. 15 is a block schematic diagram depicting how the medical device is tested while in the shipping container includes one or more of the following techniques: sensing of nonvisual radiation from the photodiode using a photodetector and a transconductance amplifier, use of an inductively coupled current loop path (with an optional breakaway section to electrically detach the LEDs), capacitive sensing of the circuitry, inductive sensing of the circuitry (without the current loop path and cutout), and/or one or more switches, e.g., a single pole double throw (SPDT) switch, to selectively connect the medical device's electrodes to the LEDs and/or the inductively coupled current loop.

FIG. 11 shows an isometric view of circuit board 72 and O-ring mounting apparatus of FIGS. 10A and 10B, additionally including a photodiode 220 (also see FIG. 12) for emitting nonvisual, e.g., ultraviolet or infrared, radiation (light) that can be externally monitored to test the functionality of the medical device 20, e.g., while it is still within a sterilized delivery package, e.g., a pouch. As shown in FIG. 15, an external monitor/generator 222 may include a photodetector 224 that is sensitive to nonvisual radiation 226 emitted by the photodiode 220. When the photodetector 224 is used in combination with a transconductance amplifier 228 or the like, the nonvisual radiation 226 which was generated in an essentially linear relationship with the current passed through the photodiode 224 is converted to an output signal 230 which essentially linearly corresponds to the output of the medical device 20 through its electrodes 32, 34. This output signal 230 may then be measured with an oscilloscope, automated test equipment, or the like, to confirm that the medical device 20 is performing within specifications (before implantation).

Figure 13A:
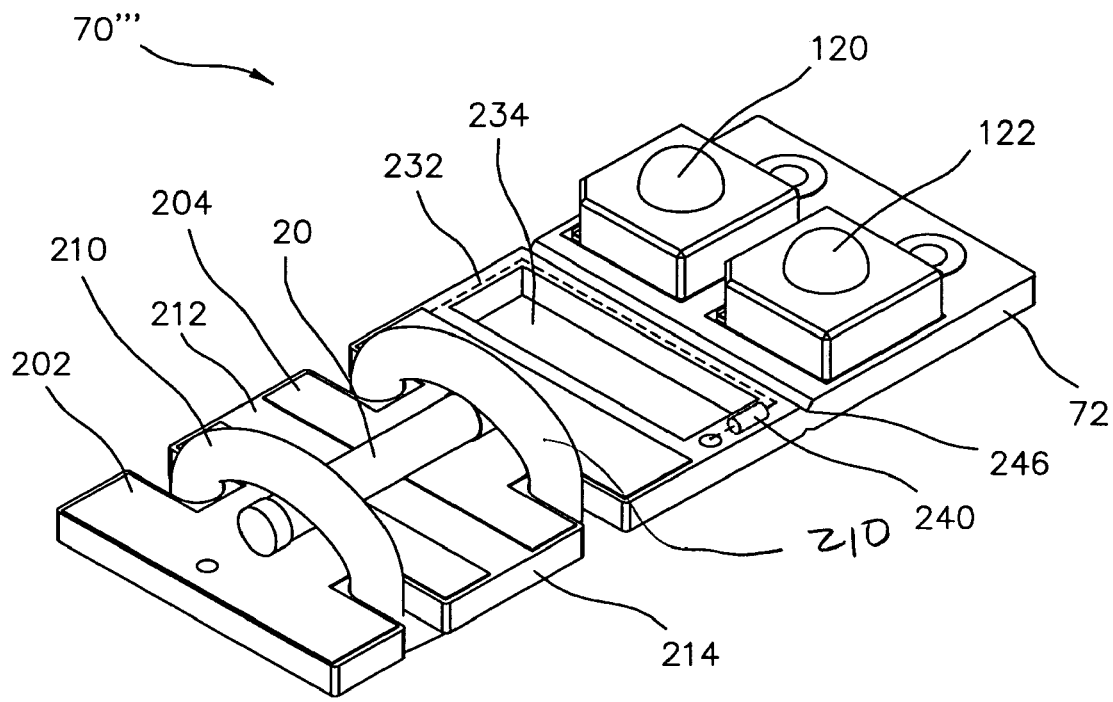
Figure 13B:
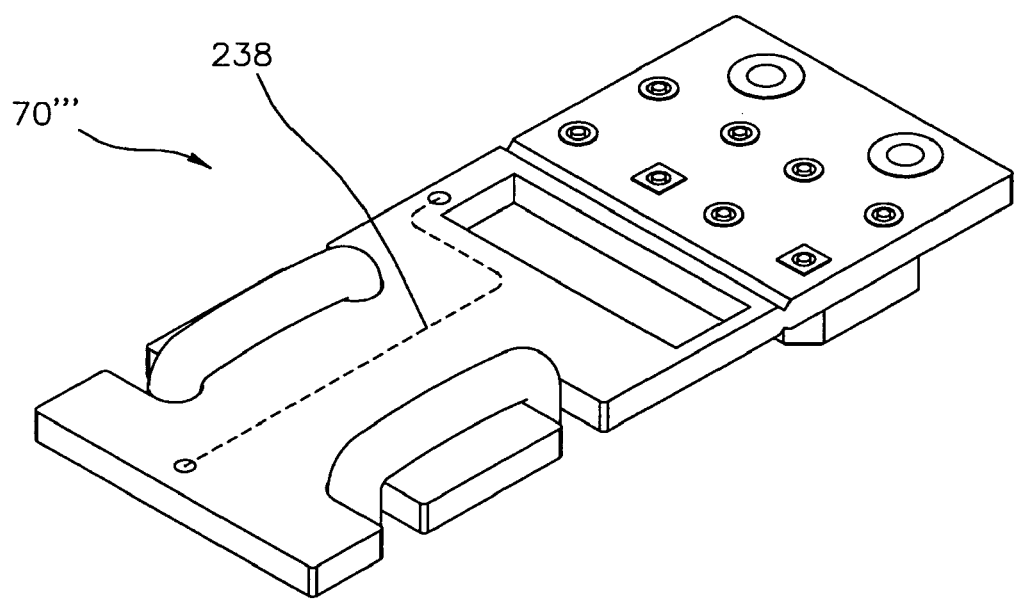

FIGS. 13A and 13B show the presence of a current loop path 232 (also shown in FIG. 12) with a cutout 234 for allowing an inductive pickup loop e.g., an oscilloscope probe loop (not shown), to pass through and thus inductively measure the current being passed between electrodes 32, 34 of the medical device 20 (via connective surfaces 202, 204 and feedthrough/back side connection path 238. Optionally, a resistor element 240, e.g., on the order of 250 ohms, is used to simulate body tissue and to avoid/limit interactions with LEDs 120, 122. Also, see FIG. 15 where photodiode 220 is essentially replaced by a short circuit and monitor/generator 222 measures/detects the operation of medical device 20 through inductive pickup loop 236.

Figure 14A:
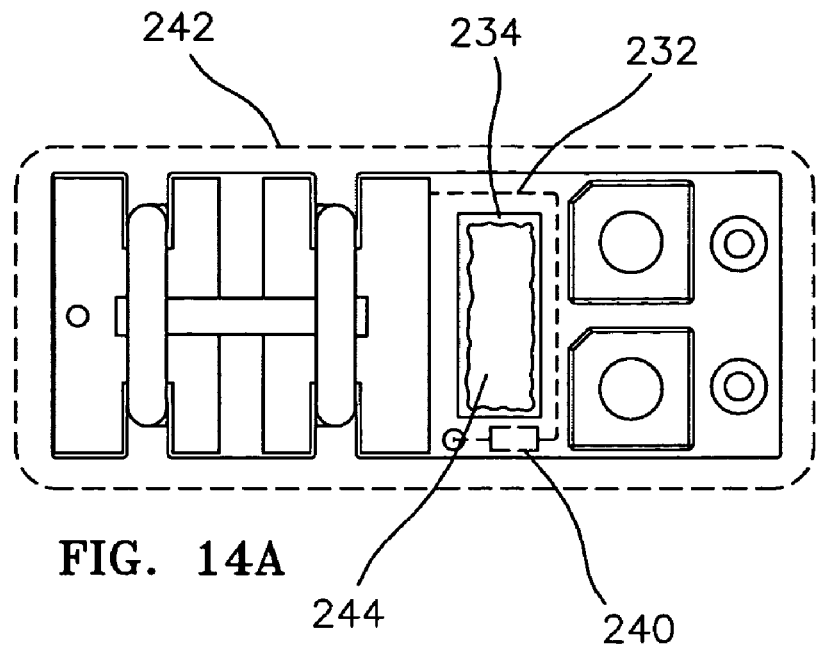
FIGS. 14A, 14B, and 14C respectively show top, side and bottom views corresponding to the embodiment of FIGS. 13A and 13B sealed within a sterile pouch having a compliant cutout formed thereon. Additionally, the use of an optional breakaway section is shown to remove the LED portion and thus improve the functionality of the current loop path (by removing interactions with the LED path).
Figure 14B:
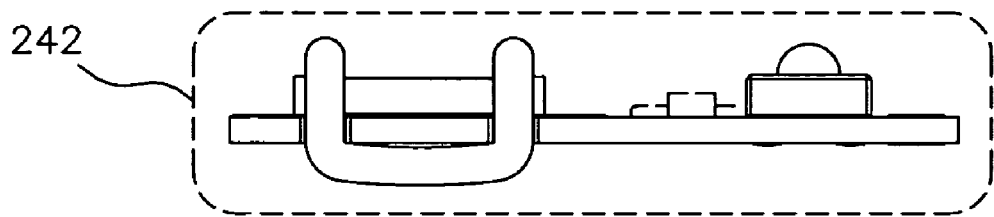
Figure 14C:
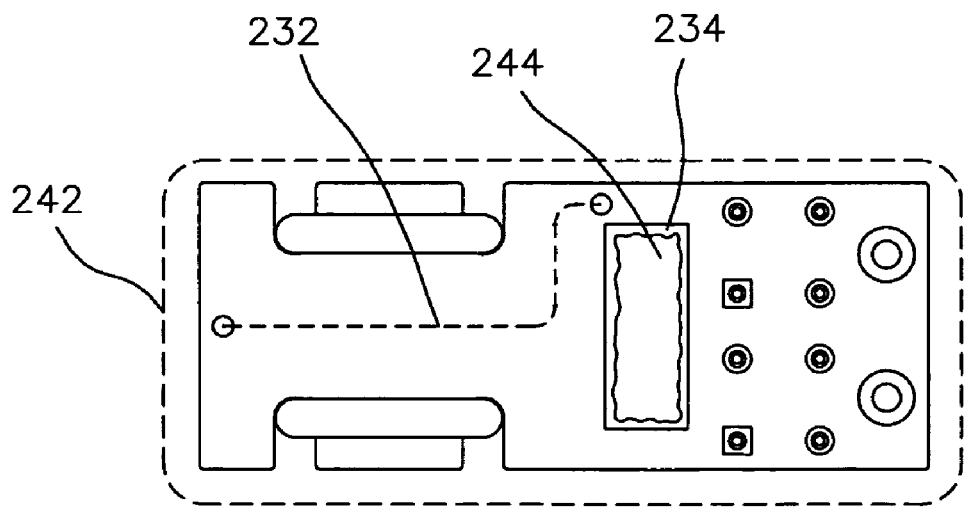

FIGS. 14A, 14B, and 14C respectively show top, side and bottom views of the embodiment of FIGS. 13A and 13B sealed within a sterile pouch 242 having a compliant, and thus somewhat smaller cutout 244 formed thereon. An inductive pickup loop, such as an oscilloscope probe loop (not shown), may thus pass through sterile pouch cutout 244 which in turn is within cutout 234, without breaking the sterile seal of pouch 242.

Ideally, however, the LEDs 120, 122 are not present when the current loop path 232 is used. Accordingly, an optional breakaway portion path 246 may be implemented on the circuit board 72 to permanently disconnect the LEDs 120, 122 when they are no longer needed. Thus, in this mode the LEDs 120, 122 would be used as an initial "go/no go" test and then, as a final before implantation test, the LEDs 120, 122 would be disconnected via breakaway portion path 246 before final measurement testing via current loop path 232. Alternatively, a single pole double throw (SPDT) switch 248 could be used to alternatively enable LEDs 120, 122 or current loop path 232 (see FIG. 15). Such a switch could either be a discrete device soldered to the circuit board 72 or could be one or more metallic appendages that extend from the circuit board 72 to form one or more electrical switches to create the functional equivalent of switch 248.

As an additional alternative (see FIG. 15), a pair of capacitive plates 250, 252 coupled to the monitor/generator 222 could be used to detect operation of the medical device 20. Alternatively, capacitive plates 250, 252 could be replaced with one or more coils or a surrounding coil to similarly detect operation of the medical device 20. In such a case, element 240 may be replaced with an inductor. Since such alternatives would tend to block passage of an RF signal into the medical device (needed for RF powered stimulators), this alternative is best used with a battery powered stimulator.

Finally, the previously referenced implantable medical devices (see, for example, U.S. Pat. Nos. 6,164,284; 6,185,452; 6,208,894; 6,315,721; and 6,472,991) may also be able to operate as a sensor and thus sense neuro-muscular signals via its electrodes 32, 34. To test functionality of such devices operating as a sensor, one must provide an electrical signal to electrodes 32, 34 and communicate (typically via an RF signal) with the medical device 20 to confirm proper detection of the input voltage signal. In this mode (see FIG. 15), the monitor/generator 222 operates as a pulse generator and puts out various programmable frequency and amplitude signals through pickup loop 236 which is inductively provided through current loop path 232 to electrodes 32, 34 of the medical device 20. In response, medical device 20 communicates with controller 164 to determine functionality of the medical device 20. Optionally, controller 164 may communicate with monitor/generator 222 (shown as a dashed path) to coordinate comparisons of the expected and actual received signals.

Figure 16A:
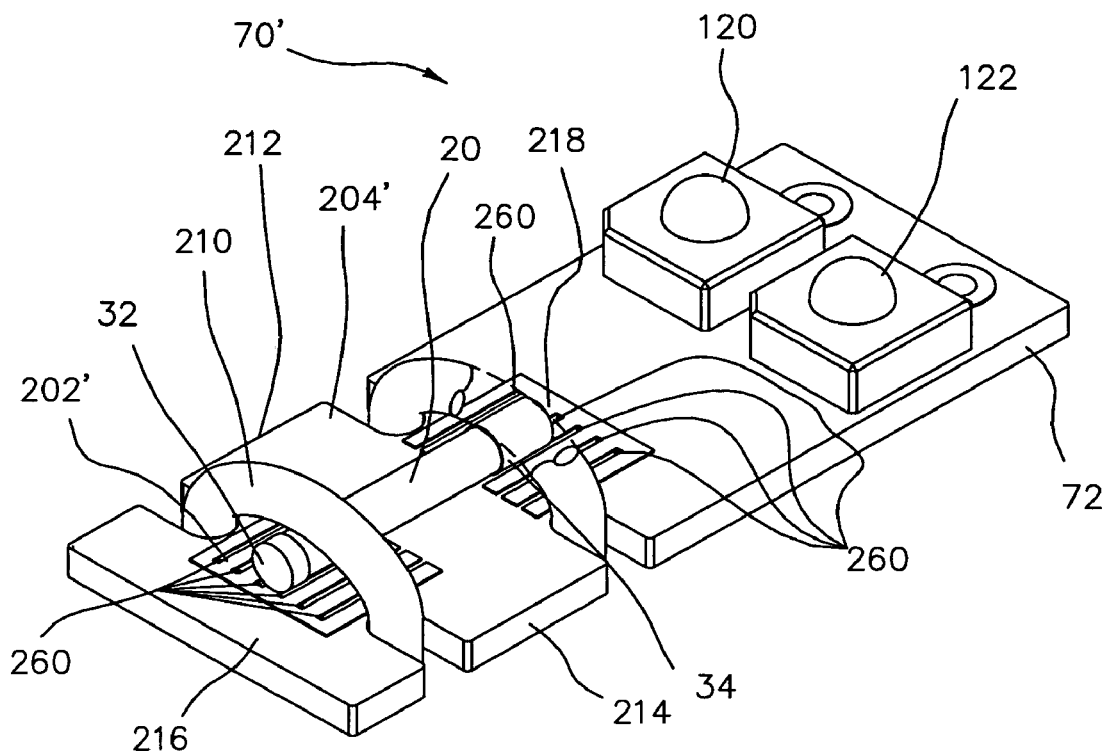
FIGS. 16A-16D are alternative embodiments of that previously shown in FIG. 10A wherein the connective surfaces are formed with slots to reduce eddy currents and thereby reduce signal loss to the implantable medical device of the magnetic and/or electromagnetic signals while it is held by the protection apparatus.
Figure 16B:
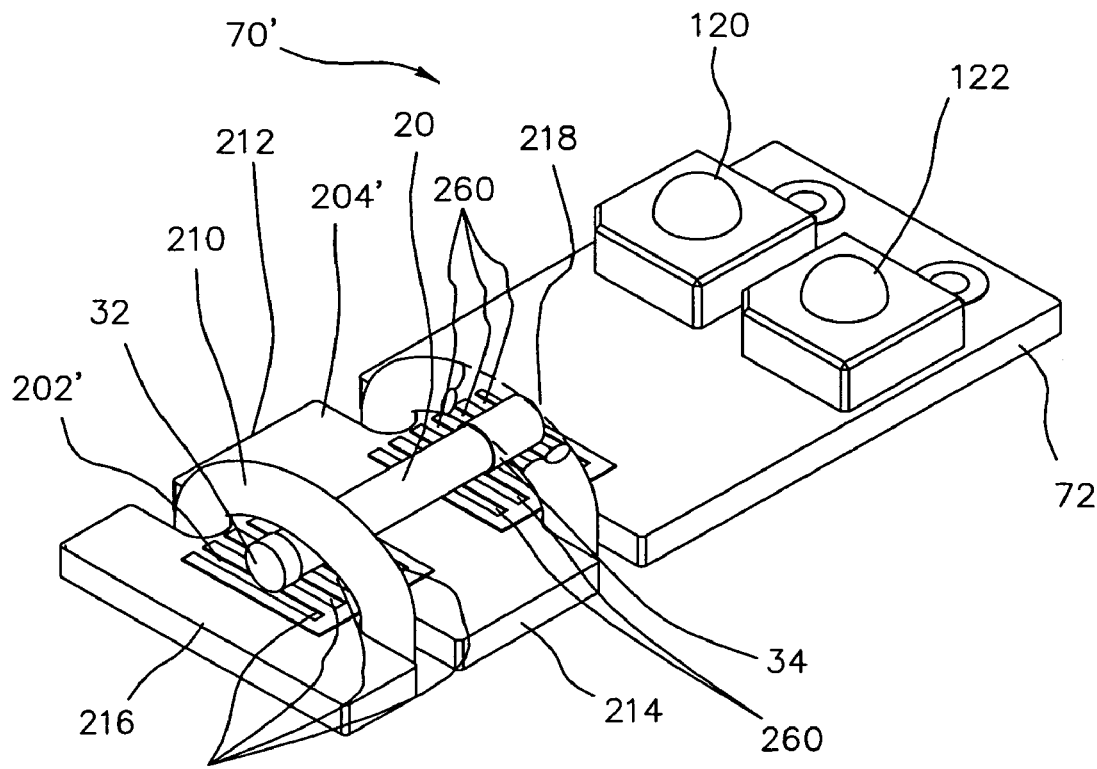
Figure 16C:
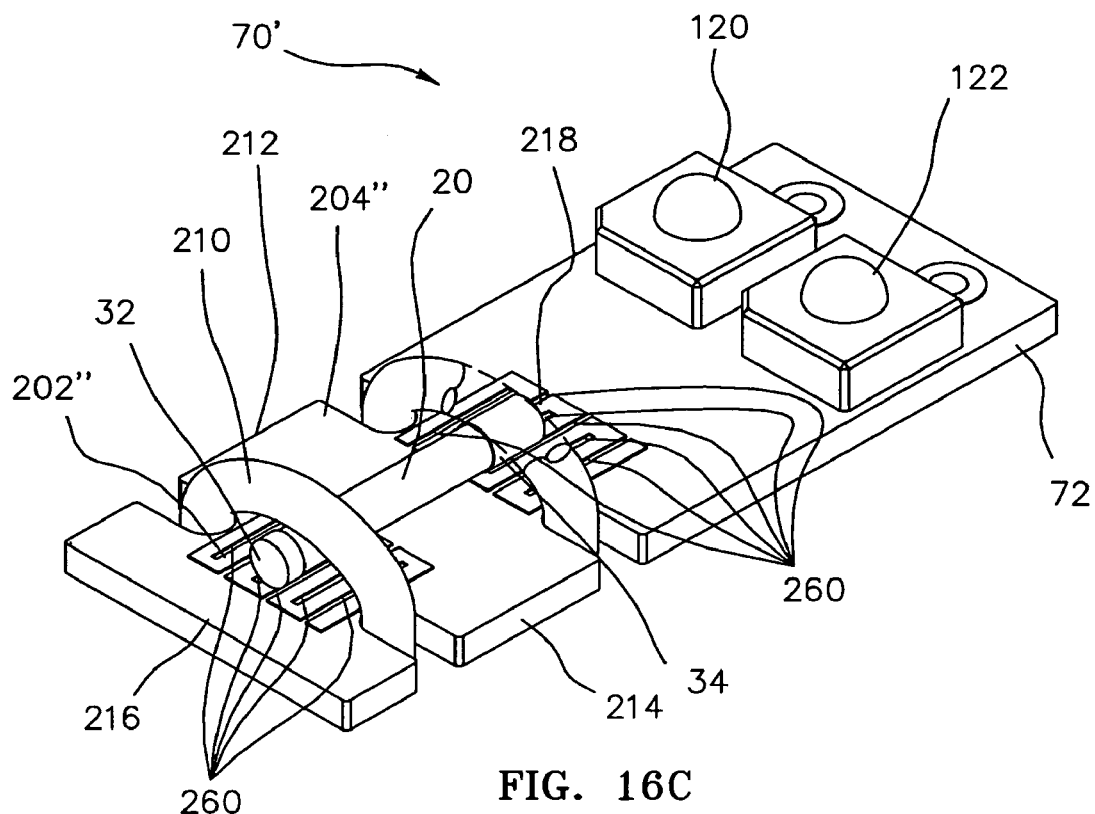
Figure 16D:
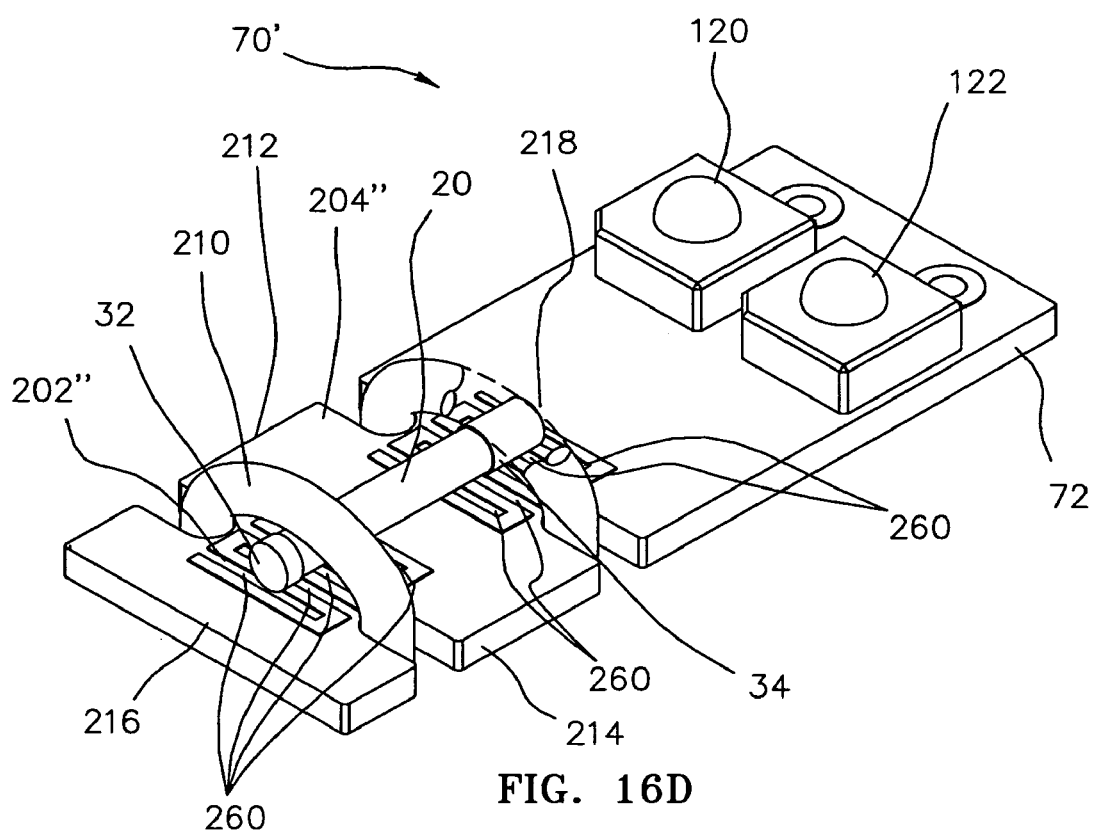

In the previously shown examples, e.g., FIGS. 10A, 11, and 13, the connective surfaces are shown as solid plated surfaces. This configuration can result in heating of the connective surfaces and some loss of the magnetic/electromagnetic signals being sent to the implantable device 20 from power source 160 and/or controller 164 (see FIGS. 8 and 15), e.g., resulting from eddy currents on the connective surfaces, when the implantable medical device 20 is held by the protection apparatus 70 (and in particular 70' [see FIGS. 10A AND 10B], 70'' [see FIG. 11] or 70''' [see FIGS. 13A and 13B]). Accordingly, FIGS. 16A-16D are alternative embodiments of that previously shown, e.g., in FIG. 10A, wherein the connective surfaces are formed with slots or serpentine paths to reduce eddy currents and thereby reduce signal loss to the implantable medical device 20 of the magnetic and/or electromagnetic signals while it is held by the protection apparatus 70. In particular, FIGS. 16A and 16B show connective surfaces 202' and 204' formed as comb-shaped connective surfaces having a plurality of slots 260 to minimize eddy currents. Alternatively, FIGS. 16C and 16D show connective surfaces 202'' and 204'' formed from serpentine paths that similarly form slots 260 in the surface to minimize eddy currents.

Although a specific embodiment of the invention has been described, it is recognized that variations and modifications will readily occur to those skilled in the art coming within the intended spirit and scope of the present invention as defined by the appended claims. For example, while the aforedescribed apparatus 70 shown in FIG. 4 is particularly suited for use with the exemplary small, cylindrical device of FIG. 1, the present invention includes the use of the aforedescribed protection circuitry with other differently shaped medical devices having two or more electrodes. In such cases, the mounting means would be adjusted accordingly to accommodate the particular device. In particular, the O-ring embodiments of FIGS. 9A, 9B, 10A, 10B, 11, 13A, 13B, 14A, 14B and 14C are particularly adapt at retaining non-cylindrical, e.g., square, triangular, hexagonal, etc., shaped medical devices in the protection apparatus of the present invention. Additionally, it should be noted that while current loop path 232 is shown graphically as a single loop (see, e.g., FIG. 13A), this is primarily to simplify the graphical depiction of this path and embodiments are intended to also include multi-looped paths. Advantageously, multi-looped embodiments will facilitate transmission and/or reception of inductively radiated signals. Finally, it is noted that a negative capacity preamp, i.e., an amplifier having a capacitor for negative feedback, could be used within the monitor/generator to pick up an electrostatic signal from the medical device and/or the medical device/protection apparatus combination and thus detect/monitor the operation of the medical device.

What is claimed is:

1. In combination with a medical device configured to be implanted in a patient's body and an external monitor/generator for functionally testing the medical device, the medical device including a housing containing electronic circuitry having output and input capability connected to first and second electrodes extending exteriorly from the housing, an apparatus for use with the medical device prior to it being implanted, said apparatus comprising:

a dielectric substrate carrying spaced first and second connective surfaces, each of said connective surfaces being configured to electrically contact one of the electrodes of the medical device;

at least one connection element comprising at least one O-ring for retaining the first and second electrodes of the medical device in physical and electrical contact with said first and second connective surfaces;

a test/protection circuit carried by said substrate electrically connected between said first and second connective surfaces, wherein said test/protection circuit comprises a current loop suitable for inductively receiving a variable magnetic field generated by the external monitor/generator to thereby functionally test the input capability of the electronic circuitry of the medical device;

wherein said apparatus is configured to be separated from the medical device before implantation.

2. The apparatus of claim 1 wherein said at least one connection element comprises first and second conductive clips mounted on said dielectric substrate for capturing and retaining the first and second electrodes of the medical device.

3. The apparatus of claim 1 wherein said at least one O-ring is formed of medical grade silicone.

4. The apparatus of claim 1 wherein said at least one connection element comprises a single O-ring and said dielectric substrate comprises a circuit board that includes a pair of retaining lips for capturing the single O-ring and wherein the medical device is retainable between the single O-ring and said circuit board.

5. The apparatus of claim 1 wherein said dielectric substrate is a circuit board formed of polyimide.

6. The apparatus of claim 1 wherein said diode is a photodiode suitable for emitting nonvisual light in response to current therethrough.

7. The apparatus of claim 1 wherein said dielectric substrate has a substrate cutout surrounded by said current loop to enable an externally provided inductive pickup loop to pass through said cutout.

8. The apparatus of claim 7 additionally comprising a sterilization pouch wherein said sterilization pouch includes a pouch cutout conforming to said substrate cutout to enable an externally provided inductive pickup loop to pass through said substrate and pouch cutouts.

9. The apparatus of claim 1 additionally comprising selection means for selecting and/or deselecting a desired test/protection circuit.

10. The apparatus of claim 1 wherein said first and second connective surfaces are formed to minimize eddy currents.

11. The apparatus of claim 10 wherein said first and second connective surfaces are comb-shaped.

12. The apparatus of claim 10 wherein said first and second connective surfaces are formed from serpentine paths.

13. A method of functionally testing an implantable medical device prior to implantation, the device comprising a housing containing electronic circuitry connected between first and second electrodes extending exteriorly from the housing, said method comprising:

providing first and second contacts on a substrate for electrically contacting the first and second electrodes;

providing at least one connection element for retaining the first and second electrodes of the medical device in physical and electrical contact with said first and second contacts; and providing a current loop between said first and second contacts suitable for inductively receiving a variable magnetic field generated by an external monitor/generator to thereby functionally test the input capability of the electronic circuitry of the medical device; wherein said apparatus is configured to be separated from the medical device before implantation.

14. The method of claim 13 wherein the step of providing a current loop path between said first and second contacts is selected from the group of:

(a) providing a current loop between said first and second contacts suitable for inductively radiating a variable magnetic field corresponding to current flowing between the first and second electrodes of the medical device, wherein said magnetic field is detectable by an external monitor/generator to thereby functionally test the output capability of the electronic circuitry of the medical device;

(b) providing at least one diode electrically connected between said first and second contacts to emit light corresponding to current flowing between the first and second electrodes of the medical device, wherein the light is detectable by an external monitor generator to thereby functionally test the output capability of the electronic circuitry medical device; and (c) providing a receiving current loop between said first and second contacts suitable for inductively receiving a variable magnetic field generated by an external monitor/generator to thereby functionally test the input capability of the electronic circuitry of the medical device.

15. The method of claim 13 further including the steps of:
providing a sterilization pouch;
placing the device within the sterilization pouch; and
sterilizing the device while in said sterilization pouch.

16. The method of claim 15 further including the steps of:
forming said current loop path on said substrate having an inner cutout;
providing a sterilization pouch having an outer cutout conforming to said inner cutout;
placing the device within the sterilization pouch; wherein said conforming inner and outer cutouts enable an externally provided inductive pickup loop to pass therein and provide a signal from an externally provided monitor/generator; and
sterilizing the device while in said sterilization pouch.

17. The method of claim 13 further including:
applying an activation signal to the device while in said shipping container; and
monitoring the emissions corresponding to the medical device in response to the application of said activation signal wherein the monitoring step is selected from the group of:
monitoring electrostatic emissions
monitoring electromagnetic emissions; and
monitoring capacitive changes.

18. The method of claim 17 wherein said step of applying an activation signal comprises providing wireless communicating energy to the electronic circuitry in the housing.

19. The method of claim 17 wherein said step of monitoring the emissions in response to the application of said activation signal comprises use of a negative capacity preamp to pick up a signal from the medical device.

20. The method of claim 13 wherein the step of providing first and second contacts includes forming said contacts to minimize eddy currents.

21. The method of claim 20 wherein the step of forming said contacts to minimize eddy currents comprises forming said contacts in a comb-shaped manner.

22. The method of claim 20 wherein the step of forming said contacts to minimize eddy currents comprises forming said contacts in a serpentine manner.

* * * * *